United States Patent
Santra et al.

(10) Patent No.: US 10,894,910 B2
(45) Date of Patent: Jan. 19, 2021

(54) ADDITIVES FOR OIL AND GAS DRILLING AND PRODUCTION

(71) Applicant: SAUDI ARABIAN OIL COMPANY, Dhahran (SA)

(72) Inventors: Ashok Santra, Houston, TX (US); Matthew Gary Hilfiger, Houston, TX (US)

(73) Assignee: SAUDI ARABIAN OIL COMPANY

(*) Notice: Subject to any disclaimer, the term of this patent is extended or adjusted under 35 U.S.C. 154(b) by 87 days.

(21) Appl. No.: 16/176,584

(22) Filed: Oct. 31, 2018

(65) Prior Publication Data

US 2020/0131423 A1 Apr. 30, 2020

(51) Int. Cl.

| | |
|---|---|
| C09K 8/06 | (2006.01) |
| C07C 13/04 | (2006.01) |
| C07C 215/40 | (2006.01) |
| C09K 8/54 | (2006.01) |
| C09K 8/82 | (2006.01) |
| C09K 8/86 | (2006.01) |
| E21B 41/02 | (2006.01) |
| C07C 213/04 | (2006.01) |
| C09K 8/34 | (2006.01) |

(52) U.S. Cl.
CPC .............. *C09K 8/06* (2013.01); *C07C 213/04* (2013.01); *C07C 215/40* (2013.01); *C09K 8/34* (2013.01); *C09K 8/54* (2013.01); *C09K 8/82* (2013.01); *C09K 8/86* (2013.01); *E21B 41/02* (2013.01)

(58) Field of Classification Search
None
See application file for complete search history.

(56) References Cited

U.S. PATENT DOCUMENTS

| | | | |
|---|---|---|---|
| 3,079,221 A | 2/1963 | Andersen | |
| 3,829,506 A | 8/1974 | Schmolka et al. | |
| 7,160,507 B2 | 1/2007 | Dahlmann et al. | |
| 8,999,315 B2 | 4/2015 | Henry et al. | |
| 9,637,679 B2 | 5/2017 | Qu et al. | |
| 2011/0071056 A1 | 3/2011 | Saini et al. | |
| 2013/0196884 A1 | 8/2013 | Kakadjian et al. | |
| 2017/0190952 A1 | 7/2017 | Qu et al. | |

FOREIGN PATENT DOCUMENTS

| | | |
|---|---|---|
| CN | 10359545 A | 1/2014 |
| WO | 2017112721 A1 | 6/2017 |

OTHER PUBLICATIONS

STIC search (Year: 2020).*
International Search Report and Written Opinion for related PCT application PCT/US2019/059011 dated Jan. 31, 2020.
Lippur et al., "Synthesis of (2S,2'S)-bimorpholine N,N'-quaternary salts as chiral phase transfer catalysts", Tetrahedron: Asymmetry, 2007, pp. 137-141, Elsevier Ltd.
Marson et al., Synthesis of (3S,3S',4S,4S')-1,1'-ethylenedipyrrolidine-3,3',4,4'-tetraol and related diamino diols: donor-acceptro hydrogen-bonding motifs of the C2 symmetric 3,4-dihydroxypyrrolidine unit, Tetrahedron: Asymmetry, 2005, pp. 2799-2809.

* cited by examiner

Primary Examiner — Jeffrey D Washville
(74) Attorney, Agent, or Firm — Bracewell LLP; Constance R. Rhebergen

(57) ABSTRACT

A quaternary amine composition selected from the group consisting of Formula I, Formula II, Formula III, and combinations of the same. A method of synthesizing a quaternary amine composition comprising the steps of reacting an alkoxylated dimer diamine with a methyl halogen, where the methyl halogen is selected from the group consisting of methyl chloride, methyl iodine, and combinations of the same; and allowing the reaction to proceed to produce the quaternary amine composition, the quaternary amine composition selected from the group consisting of Formula I, Formula II, Formula III, and combinations of the same. A method of treating a well comprising the steps of introducing an additive-containing well fluid to a well, where the additive-containing well fluid comprises a quaternary amine composition and a well fluid, allowing the additive-containing well fluid to interact with the well, and treating the well with the additive-containing fluid.

8 Claims, No Drawings

ADDITIVES FOR OIL AND GAS DRILLING AND PRODUCTION

TECHNICAL FIELD

Disclosed are compositions for use in oil and gas drilling and production. More specifically, embodiments related to compositions for use as additives in drilling and production fluids are disclosed.

BACKGROUND

Drilling and production fluids tend to be a mixture of multiple components, each enhancing the functionality of the fluids. In particular, components can be added to improve the interaction between the fluid and the drilling tools, the interaction between the fluid and the formation, and the stability of the fluid itself.

There are classes of components that can provide multi-functionality to drilling and production fluids. For example, film forming and cationic molecules based on amine surfactants, such alkyl pyridines, tallow amines, polyamines, and polyether amines, for example, have long been used to provide multiple forms of functionality.

Amines and quaternary amine surfactants form film(s) or protective layer(s) on casing, drill strings, drilling equipment, and product equipment by chemically or physically adsorbing on the surface of the equipment. The interaction between an amine group and the metal/metal-oxide surface is relatively weak because there is no net positive charge on it. The interaction strength between the surface and the quaternary amine surfactant with a net positive charge is mostly electrostatic in nature. The charge density on the quaternary amine group determines how strongly the molecule is bound to the surface, with greater binding strength associated with increased corrosion resistance. Stronger adsorption strength improves the film-forming efficiency, including at elevated temperatures when the kinetic energy of the molecules increases making the equipment labile.

SUMMARY

Disclosed are compositions for use in oil and gas drilling and production. More specifically, embodiments related to compositions for use as additives in drilling and production fluids are disclosed.

In a first aspect, a quaternary amine composition is provided. The quaternary amine composition is selected from the group consisting of Formula I, Formula II, Formula III, and combinations of the same, where Formula I is:

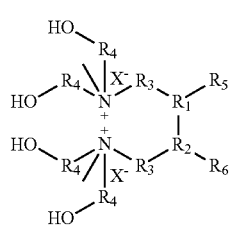

(I)

where each of $R_1$ and $R_2$ is selected from the group consisting of a carbon atom (C—) and a carbon bonded to a hydrogen (—CH), each $R_3$ is selected from the group consisting of a saturated aliphatic hydrocarbyl and an unsaturated aliphatic hydrocarbyl, each $R_4$ is selected from the group consisting of an acyclic hydrocarbyl and an acyclic heterohydrocarbyl, each of $R_5$ and $R_6$ is selected from the group consisting of a saturated acyclic hydrocarbyl and an unsaturated acyclic hydrocarbyl, and X is selected from the group consisting of an iodine ion (I—), a chlorine ion (Cl—), and combinations of the same;

where Formula II is:

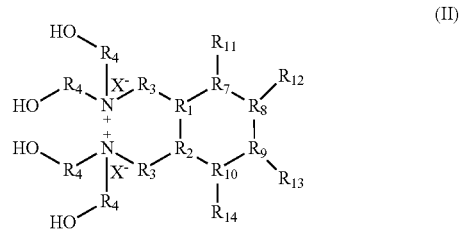

(II)

where each of $R_7$, $R_8$, $R_9$, and $R_{10}$ is selected from the group consisting of a C— and a —CH, each of $R_{11}$, $R_{12}$, $R_{13}$, and $R_{14}$ is selected from the group consisting of a hydrogen atom (H—), an aliphatic hydrocarbyl group, and a substituted aliphatic hydrocarbyl group;

where Formula III is:

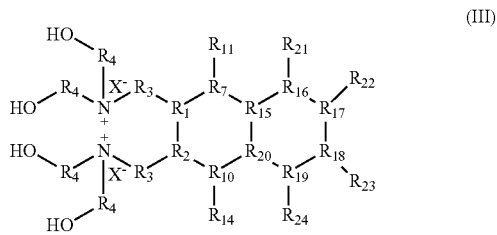

(III)

where $R_{15}$ is selected from the group consisting of a C—, a —CH, and a carbon bonded to $R_{25}$ (—$CR_{25}$), each of $R_{16}$, $R_{17}$, $R_{18}$, and $R_{19}$ is selected from the group consisting of a C— and a —CH, $R_{20}$ is selected from the group consisting of a C—, a —CH, and a carbon bonded to $R_{26}$ (—$CR_{26}$), each of $R_{21}$, $R_{22}$, $R_{23}$, and $R_{24}$ can include a hydrogen atom (H—), an aliphatic hydrocarbyl group, and a substituted aliphatic hydrocarbyl group, $R_{25}$ is selected from the group consisting of an aliphatic hydrocarbyl group, a substituted aliphatic hydrocarbyl group, and combinations of the same, $R_{26}$ is selected from the group consisting of an aliphatic hydrocarbyl group, a substituted aliphatic hydrocarbyl group, and combinations of the same.

In certain aspects, $R_3$ is selected from the group consisting of a saturated $C_2$-$C_{20}$ acyclic hydrocarbyl and an unsaturated $C_2$-$C_{20}$ acyclic hydrocarbyl. In certain aspects, at least one of $R_5$ and $R_6$ is an unsaturated $C_2$-$C_{20}$ acyclic hydrocarbyl. In certain aspects, both $R_5$ and $R_6$ are unsaturated $C_2$-$C_{20}$ acyclic hydrocarbyls. In certain aspects, $R_3$ is a saturated $C_5$-$C_{10}$ acyclic hydrocarbyl and each of $R_5$ and $R_6$ is a $C_5$-$C_{15}$ acyclic hydrocarbyl. In certain aspects, where the composition includes Formula II, where a ring formed by $R_1$, $R_2$, $R_7$, $R_8$, $R_9$, and $R_{10}$ is selected from the group consisting of a cyclohexane, a cyclohexene, a cyclohexadiene, and a benzene. In certain aspects, Formula II is selected from the group consisting of Formula IV, Formula V, Formula VI, Formula VII, and Formula VIII, where the compositions of Formulas IV-Formula VIII are:

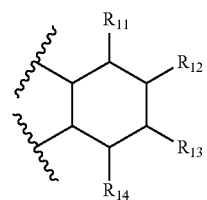
(IV)

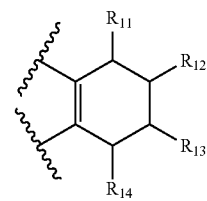
(V)

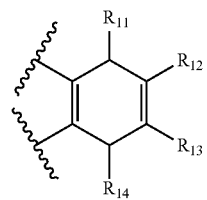
(VI)

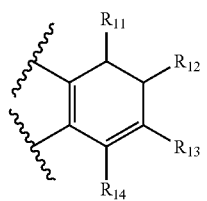
(VII)

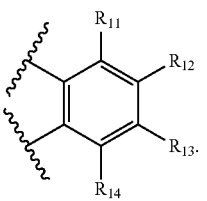
(VIII)

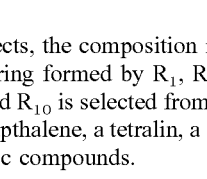

In certain aspects, the composition includes Formula III, where a double ring formed by $R_1$, $R_2$, $R_7$, $R_{15}$, $R_{16}$, $R_{17}$, $R_{18}$, $R_{19}$, $R_{20}$, and $R_{10}$ is selected from the group consisting of a decahydronapthalene, a tetralin, a dialin, a naphthalene, and other bicyclic compounds.

In certain aspects, Formula III is selected from the group consisting of Formula IX, Formula X, Formula XI, Formula XII, Formula XIII, Formula XIV, Formula XV, Formula XVI, Formula XVII, Formula XVIII, Formula XIX, and Formula XX where the compositions of Formulas IX-Formula XX are:

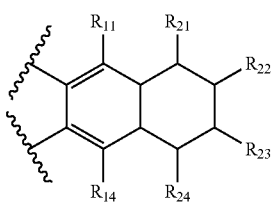
(IX)

-continued

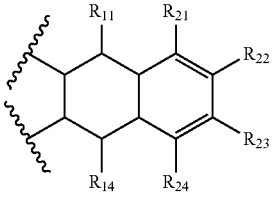
(X)

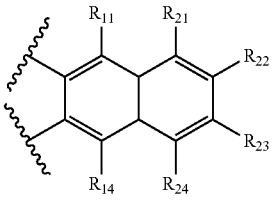
(XI)

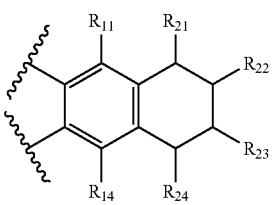
(XII)

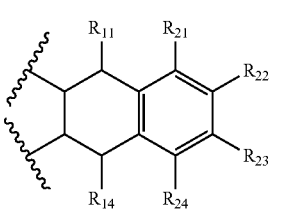
(XIII)

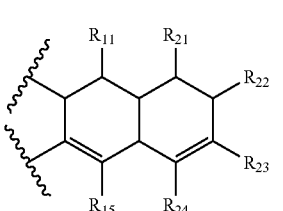
(XIV)

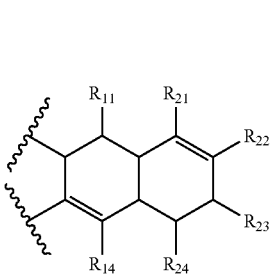
(XV)

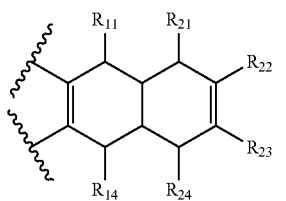
(XVI)

-continued

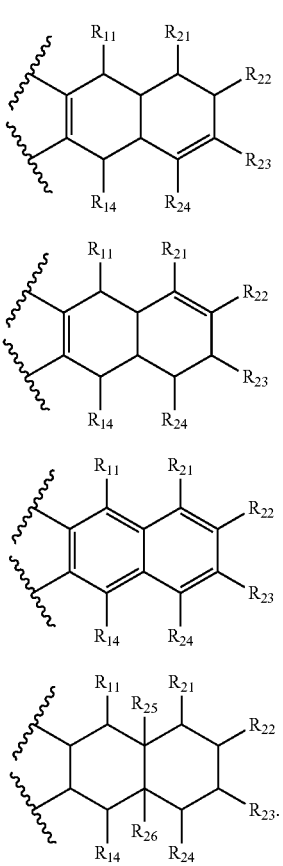

(XVII)

(XVIII)

(XIX)

(XX)

In certain aspects, the substituted aliphatic hydrocarbyl group includes a replacement group, where the replacement group is selected from the group consisting of a hydroxyl group, an aminoalkyl group, an alkoxyl group, an alkylthio group, an amino group, a halo group, a haloalkyl group, a silyl group, a phosphoryl group, a sulfonyl group, and combinations of the same.

In certain aspects, the quaternary amine composition includes Formula XXIII:

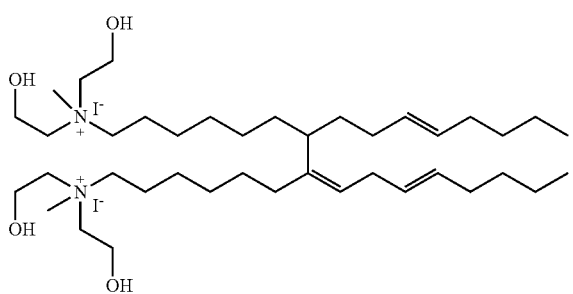

(XXVII)

where the quaternary amine composition takes the form of Formula I; where $R_1$ is a carbon bonded to a hydrogen (—CH), $R_2$ is a carbon atom (C—), each $R_3$ is a saturated $C_6$ acyclic hydrocarbyl, $R_5$ is an unsaturated $C_8$ acyclic hydrocarbyl, $R_6$ is an unsaturated $C_8$ acyclic hydrocarbyl, and each $R_4$ is a saturated $C_2$ acyclic hydrocarbyl.

In a second aspect, a method of synthesizing a quaternary amine composition is provided. The method includes the steps of reacting an alkoxylated dimer diamine with a methyl halogen, where the methyl halogen is selected from the group consisting of methyl chloride, methyl iodine, and combinations of the same, and allowing the reaction to proceed to produce the quaternary amine composition, the quaternary amine composition selected from the group consisting of Formula I, Formula II, Formula III, and combinations of the same.

In certain aspects, the step of reacting the alkoxylated dimer diamine with the methyl halogen is at ambient conditions.

In a third aspect, a method of treating a well is provided. The method includes the steps of introducing an additive-containing well fluid to a well, where the additive-containing well fluid includes a quaternary amine composition, where the additive-containing well fluid includes a well fluid, allowing the additive-containing well fluid to interact with the well, where the additive-containing well fluid is operable to treat the well, and treating the well with the additive-containing fluid.

In a third aspect, the quaternary amine composition is selected from the group consisting of Formula I, Formula II, Formula III, and combinations of the same.

In certain aspects, the well fluid is selected from the group consisting of an aqueous-based fluid, an oil-based fluid, and combinations of the same. In certain aspects, the step of treating a well can be selected from the group consisting of reducing corrosion, stabilizing clays in the well, stabilizing an emulsion, and combinations of the same.

DETAILED DESCRIPTION

While the scope will be described with several embodiments, it is understood that one of ordinary skill in the relevant art will appreciate that many examples, variations and alterations to the apparatus and methods described are within the scope and spirit of the embodiments. Accordingly, the embodiments described here are set forth without any loss of generality, and without imposing limitations. Those of skill in the art understand that the scope includes all possible combinations and uses of particular features described in the specification. In both the drawings and the detailed description, like numbers refer to like elements throughout.

The quaternary amine compositions described here can be used as additives in a drilling and production fluids. The quaternary amine compositions described here are amine oxide quaternary compounds with a germinal structure, meaning the compounds possess two polar groups and two hydrophobic tails. As noted, the charge density on the quaternary amine group determines how strongly the molecule is bound to the surface, with greater binding strength associated with increased corrosion resistance. Non-germinal quaternary amine surfactants have weaker adsorption, or binding strength, compared to the germinal-containing surfactants. Advantageously, the germinal structure of the quaternary amine compositions described here have increased adsorption strength compared to non-germinal-containing surfactants. Advantageously, quaternary amine compositions have improved film-forming efficiency, including at wellbore temperatures, where the temperatures are such that the kinetic energy of the molecules increases making the equipment labile as compared to non-germinal-containing surfactants.

As used here, "acyclic" refers to a hydrocarbon or hydrocarbon functional group that does not form a ring. Acyclic compounds can be saturated or unsaturated. Acyclic compounds can be straight-chain or branched-chain. Acyclic can be used to describe acyclic hydrocarbons, acyclic hydrocarbyls, and acyclic heterohydrocarbyls.

As used here, "aliphatic" refers to the class of hydrocarbons or hydrocarbon functional groups that are not aromatics. Aliphatic hydrocarbons can by acyclic or cyclic. Aliphatic hydrocarbons can be saturated or unsaturated. An aliphatic hydrocarbyl refers to an acyclic or cyclic, saturated or unsaturated compound composed of carbon and hydrogen that is not aromatic.

As used here, "alkoxylated dimer diamine" refers to a compound having the composition of Formula XXI:

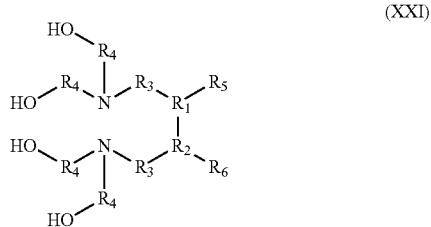

(XXI)

where $R_1$ and $R_2$ can include a carbon (—C) and a carbon bonded to a hydrogen (—CH); each $R_3$ can include an aliphatic hydrocarbyl, where each $R_3$ can be different or the same; $R_4$ can include an acyclic hydrocarbyl, an acyclic heterohydrocarbyl, and combinations of the same, where each $R_4$ can be the same; each of $R_5$ and $R_6$ can include an acyclic hydrocarbyl; and X is a halogen that can include iodine ion (I), a chlorine ion (Cl), or combinations of the same. Commonly owned U.S. patent application Ser. No. 15/860,831 filed on Jan. 3, 2018, which is incorporated by reference in its entirety, sets forth examples of alkoxylated dimer diamines that can be used to synthesize the quaternary amine compositions.

As used here, "aqueous-based fluid" refers to a water-based fluid that is used to drill a wellbore or for other wellbore activities. Aqueous-based fluids are also known as muds. Aqueous-based fluids suitable for use in the embodiments can have a salt concentration due to the presence of salt in the water-based fluid. The salt concentration can be in the range from between less than 1 pound per barrel to the saturation point. Examples of aqueous-based fluids include fresh water, deionized water, sea water, brine, and combinations of the same.

As used here, "clay stabilization" refers to inhibition of clay swelling due to clay coming in contact with water or water based fluids. Clay swelling can be due to cation exchange with the quaternary amine or by film forming.

As used here, "cyclic" refers to a hydrocarbon or hydrocarbon functional group that forms an aromatic or aliphatic hydrocarbon with at least one ring or cyclic group in its structural backbone.

As used here, "functional group" or "moiety" or "substituent" refers to an atom or grouping of molecules which can form a bond with other molecules. A functional group or moiety or substituent maintains its chemical properties or characteristics regardless of what molecule with which the functional group is bonded. As used in this application, functional groups are represented by $R_z$, where "z" represents an integer to differentiate the functional groups without implying anything about the composition of the functional group.

As used here, "hydrocarbyl" or "hydrocarbyl group" refers to a functional group composed of carbon and hydrogen. As a functional group, the hydrocarbyl is missing at least one hydrogen, where the hydrocarbyl bonds to another chemical group. As used here, a "heterohydrocarbyl" refers to a hydrocarbyl, in which one or more of the carbon atoms is substituted with a heteroatom. Heteroatoms can include oxygen (O), sulfur (S), nitrogen (N), phosphorous (P), and combinations of the same.

As used here, "saturated" refers to a hydrocarbon functional group containing only carbon-carbon single bonds. In other words, a saturated aliphatic hydrocarbyl does not contain any carbon-carbon double bonds or carbon-carbon triple bonds. A saturated acyclic hydrocarbyl group can include an alkyl group, the alkyl group is missing one hydrogen where the alkyl group bonds to another molecule.

As used here, "substituted" means replaced. In chemistry an atom or functional group is substituted when it is replaced with another atom or functional group where the molecule contains to remain intact.

As used here, "unsaturated" refers to a hydrocarbon functional group containing at least one carbon-carbon double bond or triple bond. An unsaturated acyclic hydrocarbyl group can include an alkenyl group or an alkynyl group, the alkenyl group or the alkynyl group missing one hydrogen where the alkenyl group or the alkynyl group bonds to another molecule.

As used here, "wellbore" refers to a hole drilled into a hydrocarbon-bearing formation, defined by a wellbore wall. The wellbore wall can be a face of the formation or can be formed from materials encasing the face of the formation, where the materials define wellbore. The wellbore can be in fluid communication with the hydrocarbon-bearing formation through the wellbore wall.

The quaternary amine composition can include the composition of Formula I, the composition of Formula II, the composition of Formula III, or combinations of the same. The composition of Formula I is:

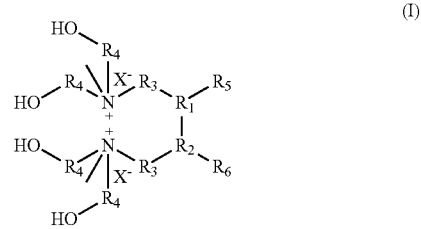

(I)

where $R_1$ and $R_2$ can include a carbon atom (C—) and a carbon bonded to a hydrogen (—CH); each $R_3$ can include an aliphatic hydrocarbyl, where each $R_3$ can be different or the same; $R_4$ can include an acyclic hydrocarbyl, an acyclic heterohydrocarbyl, and combinations of the same, where each $R_4$ can be the same; each of $R_5$ and $R_6$ can include an acyclic hydrocarbyl; and X is a halogen that can include iodine ion (I—), a chlorine ion (Cl—), and combinations of the same.

The aliphatic hydrocarbyl of $R_3$ can include a saturated aliphatic hydrocarbyl, an unsaturated aliphatic hydrocarbyl, and combinations of the same. The aliphatic hydrocarbyl of $R_3$ can include an acyclic hydrocarbyl, a cyclic hydrocarbyl, and combinations of the same. The aliphatic hydrocarbyl of $R_3$ can include a saturated $C_2$-$C_{20}$ aliphatic hydrocarbyl, alternately an unsaturated $C_2$-$C_{20}$ aliphatic hydrocarbyl, alternately a saturated $C_2$-$C_{12}$ aliphatic hydrocarbyl, alternately an unsaturated $C_2$-$C_{12}$ aliphatic hydrocarbyl, and alternately a saturated $C_5$-$C_{10}$ aliphatic hydrocarbyl. The aliphatic hydrocarbyl of $R_3$ can include a saturated $C_2$-$C_{20}$ acyclic hydrocarbyl, alternately an unsaturated $C_2$-$C_{20}$ acyclic hydrocarbyl, alternately a saturated $C_2$-$C_{12}$ acyclic hydrocarbyl, alternately an unsaturated $C_2$-$C_{12}$ acyclic hydrocarbyl, and alternately a saturated $C_5$-$C_{10}$ acyclic hydrocarbyl. In at least one embodiment, $R_3$ is a saturated aliphatic hydrocarbyl. In at least one embodiment, $R_3$ is a saturated acyclic hydrocarbyl. In at least one embodiment, $R_3$ is a saturated $C_2$-$C_9$ acyclic hydrocarbyl.

$R_4$ can be an acyclic hydrocarbyl. The acyclic hydrocarbyl of $R_4$ can include a saturated acyclic hydrocarbyl, an unsaturated acyclic hydrocarbyl, and combinations of the same. The acyclic hydrocarbyl can include a straight chain hydrocarbyl, a branched chain hydrocarbyl, and combinations of the same. The saturated acyclic hydrocarbyl has the formula $C_nH_{2n}$, where n is an integer in from 2 to 20. The unsaturated acyclic hydrocarbyl having the formula $C_nH_{2n-2x}$, where n is an integer from 2 to 20 and x is the number of double bonds in the unsaturated acyclic hydrocarbyl.

$R_4$ can be an acyclic heterohydrocarbyl. The acyclic heterohydrocarbyl of $R_4$ can include a saturated acyclic heterohydrocarbyl, an unsaturated acyclic heterohydrocarbyl, and combinations of the same. The acyclic heterohydrocarbyl can include a straight chain heterohydrocarbyl, a branched chain hydrocarbyl, and combinations of the same. In at least one embodiment, $R_4$ can be an acyclic heterohydrocarbyl, where the hetero atom is oxygen (O—) having the formula $(C_nH_{2n}O)_xC_nH_{2n}$, where n is an integer from 2 to 20, alternately an integer from 2 to 5, and alternately from 2 to 4 and x is an integer from 1 to 10, alternately an integer from 1 to 5, alternately an integer from 1 to 4, alternately an integer from 2 to 10, alternately an integer from 2 to 5, and alternately an integer from 4 to 10. In at least one embodiment, $R_4$ can be an acyclic heterohydrocarbyl, where the hetero atom is oxygen (O—) having the formula $(C_nH_{2n-2}O)_xC_nH_{2n}$, where n is an integer from 2 to 20, alternately an integer from 2 to 5, and alternately from 2 to 4 and x is an integer from 1 to 10, alternately an integer from 1 to 5, alternately an integer from 1 to 4, alternately an integer from 2 to 10, alternately an integer from 2 to 5, and alternately an integer from 4 to 10. In at least one embodiment, $R_4$ can be an acyclic heterohydrocarbyl, where the hetero atom is oxygen (O—) having the formula $(C_nH_{2n-2}O)_xC_nH_{2n}$-2, where n is an integer from 2 to 20, alternately an integer from 2 to 5, and alternately from 2 to 4 and x is an integer from 1 to 10, alternately an integer from 1 to 5, alternately an integer from 1 to 4, alternately an integer from 2 to 10, alternately an integer from 2 to 5, and alternately an integer from 4 to 10.

The $R_5$ and $R_6$ can form the hydrophobic tails of the quaternary amine composition. The quaternary amine composition can have two hydrophobic tails, alternately three hydrophobic tails, alternately four hydrophobic tails, and alternately one less hydrophobic tail than would make the quaternary amine composition insoluble in the fluid. In at least one embodiment, the quaternary amine composition contains two hydrophobic tails. In at least one embodiment, the quaternary amine composition contains three hydrophobic tails.

$R_5$ and $R_6$ can both be the same compound or class of compounds, or can be different compounds or different classes of compounds. The acyclic hydrocarbyl of $R_5$ and $R_6$ can be a saturated acyclic hydrocarbyl, an unsaturated acyclic hydrocarbyl, and combinations of the same. The acyclic hydrocarbyl of $R_5$ and $R_6$ can include a saturated $C_2$-$C_{20}$ acyclic hydrocarbyl, an unsaturated $C_2$-$C_{20}$ acyclic hydrocarbyl, a saturated $C_5$-$C_{15}$ acyclic hydrocarbyl, an unsaturated $C_5$-$C_{15}$ acyclic hydrocarbyl, a saturated $C_6$-$C_{12}$ acyclic hydrocarbyl, an unsaturated $C_6$-$C_{12}$ acyclic hydrocarbyl, and combinations of the same. In at least one embodiment, both $R_5$ and $R_6$ are acyclic hydrocarbyls, but the specific acyclic hydrocarbyls are different. In at least one embodiment, $R_5$ and $R_6$ are the same acyclic hydrocarbyls. In at least one embodiment, one of $R_5$ or $R_6$ is a saturated $C_2$-$C_{20}$ acyclic hydrocarbyl and the other is an unsaturated $C_2$-$C_{20}$ acyclic hydrocarbyl.

In at least one embodiment, $R_3$ is a saturated $C_5$-$C_{10}$ acyclic hydrocarbyl and each of $R_5$ and $R_6$ is a $C_5$-$C_{15}$ acyclic hydrocarbyl.

The hydroxyl groups bonded to the $R_4$ functional groups can be hydrophilic.

The composition of Formula II is:

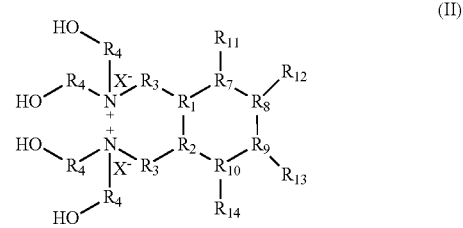

(II)

where $R_1$, $R_2$, $R_3$, $R_4$, $R_5$, $R_6$, and X are described with reference to Formula I, each of $R_7$, $R_8$, $R_9$, and $R_{10}$ can include a carbon atom (C—) and alternately a carbon bonded to a hydrogen (—CH); and each of $R_{11}$, $R_{12}$, $R_{13}$, and $R_{14}$, can include a hydrogen atom (H—), an aliphatic hydrocarbyl group, a substituted aliphatic hydrocarbyl group, an alkyl group, an aminoalkyl group, an aminoalkoxy group, a hydroxyl group, an alkoxyl group, an alkylthio group, an amino group, a halo, a haloalkyl group, a silyl group, a phosphoryl group, a sulfonyl group, and combinations of the same.

The ring of Formula II formed by $R_1$, $R_2$, $R_7$, $R_8$, $R_9$, and $R_{10}$, can include a saturated cyclic hydrocarbyl and an unsaturated cyclic hydrocarbyl. The ring of Formula II can include a cyclohexane, a cyclohexene, a cyclohexadiene, and a benzene. The ring of Formula II can include the compositions of Formulas IV to VIII:

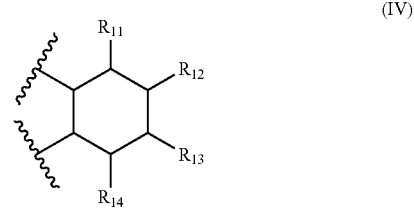

(IV)

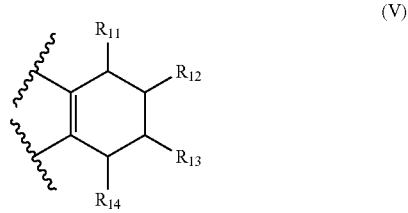

(V)

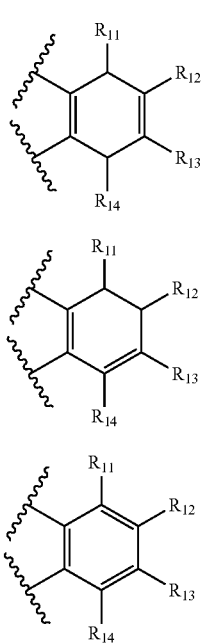

(VI)

(VII)

(VIII)

In the formulas, a wavy line "~~~~" represents the quaternary amine section of the quaternary amine composition, shown in Formula II beginning with the $R_3$ functional groups. Formula IV includes a cyclohexane, where each of $R_1$, $R_2$, $R_7$, $R_8$, $R_9$, and $R_{10}$ are a carbon bonded to a hydrogen (—CH). Formula V includes a cyclohexene, where each of $R_1$ and $R_2$ is a carbon atom (C—) and each of $R_7$, $R_8$, $R_9$, and $R_{10}$ is a carbon bonded to a hydrogen (—CH). Formula VI and Formula VII include a cyclohexadiene, where each of $R_1$ and $R_2$ is a carbon atom (C—) and two of $R_7$, $R_8$, $R_9$, and $R_{10}$ are a carbon atom (C—) and the remaining two are a carbon atom bonded to a hydrogen (—CH). Formula VIII includes a benzene, where all of $R_1$, $R_2$, $R_7$, $R_8$, $R_9$, and $R_{10}$ are a carbon atom (C—).

Returning to Formula II with reference to Formulas IV to VIII, each of the functional groups $R_{11}$, $R_{12}$, $R_{13}$, and $R_{14}$, can be a hydrogen atom (H—), an aliphatic hydrocarbyl group, a substituted aliphatic hydrocarbyl group, and combinations of the same. The aliphatic hydrocarbyl group can include a saturated acyclic hydrocarbyl and an unsaturated acyclic hydrocarbyl. The saturated acyclic hydrocarbyl can be a saturated $C_1$-$C_{100}$ acyclic hydrocarbyl, alternately a saturated $C_1$-$C_{50}$ acyclic hydrocarbyl, alternately a saturated $C_1$-$C_{25}$ acyclic hydrocarbyl, alternately a saturated $C_1$-$C_{10}$ acyclic hydrocarbyl, alternately a saturated $C_2$-$C_{20}$ acyclic hydrocarbyl, and alternately a saturated $C_2$-$C_{10}$ acyclic hydrocarbyl. The unsaturated acyclic hydrocarbyl can be an unsaturated $C_1$-$C_{100}$ acyclic hydrocarbyl, alternately an unsaturated $C_1$-$C_{50}$ acyclic hydrocarbyl, alternately an unsaturated $C_1$-$C_{25}$ acyclic hydrocarbyl, alternately an unsaturated $C_1$-$C_{10}$ acyclic hydrocarbyl, alternately an unsaturated $C_2$-$C_{20}$ acyclic hydrocarbyl, and alternately an unsaturated $C_2$-$C_{10}$ acyclic hydrocarbyl.

The substituted aliphatic hydrocarbyl group can include a substituted saturated aliphatic hydrocarbyl group and a substituted unsaturated aliphatic hydrocarbyl group. The substituted aliphatic hydrocarbyl group can include a replacement group, where the replacement group replaces one or more of the carbons in the substituted aliphatic hydrocarbyl group. The replacement group can include a hydroxyl group, an aminoalkyl group, an alkoxyl group, an alkylthio group, an amino group, a halo group, a haloalkyl group, a silyl group, a phosphoryl group, a sulfonyl group, and combinations of the same.

The composition of Formula III is:

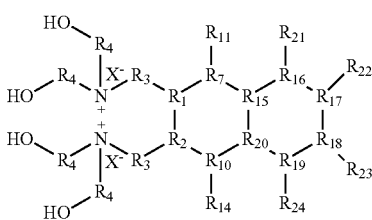

(III)

where $R_1$, $R_2$, $R_3$, $R_4$, $R_5$, $R_6$, and X are described with reference to Formula I; $R_7$, $R_{10}$, $R_{11}$, and $R_{14}$, are described with reference to Formula II; $R_{15}$ can include a carbon atom (C—), a carbon atom bonded to a hydrogen (—CH), and a carbon bonded to $R_{25}$ (—C—$R_{25}$); $R_{16}$, $R_{17}$, $R_{18}$, $R_{19}$ can include a carbon atom (C—) and a carbon bonded to a hydrogen (—CH); $R_{20}$ can include a carbon atom (C—), a carbon atom bonded to a hydrogen (—CH), and a carbon bonded to $R_{26}$ (—C—$R_{26}$); each of $R_{21}$, $R_{22}$, $R_{23}$, and $R_{24}$ can include a hydrogen atom (H—), an aliphatic hydrocarbyl group, a substituted aliphatic hydrocarbyl group and combinations of the same; each of $R_{25}$ and $R_{26}$ can include an aliphatic hydrocarbyl group, a substituted aliphatic hydrocarbyl group and combinations of the same.

The double ring of Formula III formed by $R_1$, $R_2$, $R_7$, $R_{15}$, $R_{16}$, $R_{17}$, $R_{18}$, $R_{19}$, $R_{20}$, and $R_{10}$, can include a saturated cyclic hydrocarbyl, an unsaturated cyclic hydrocarbyl, and combinations of the same. While the double ring of Formula III is shown such that the two rings are connected between the $R_{15}$ and $R_{20}$ moieties, one of skill in the art can appreciate that the second ring can be shifted, such that the two rings are connected between $R_7$ and $R_{15}$ such that the ring is formed from $R_7$, $R_{16}$, $R_{17}$, $R_{18}$, $R_{19}$, and $R_{15}$, alternately between $R_{20}$ and $R_{10}$ such that the ring is formed from $R_{20}$, $R_{16}$, $R_{17}$, $R_{18}$, $R_{19}$, and $R_{10}$. The double ring of Formula III can include a decahydronapthalene, a tetralin, a dialin, a naphthalene, and other bicyclic compounds. The ring of Formula III can include the compositions of Formulas IX to XX:

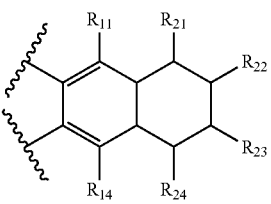

(IX)

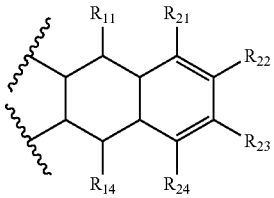

(X)

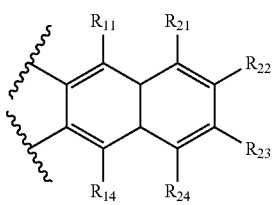

(XI)

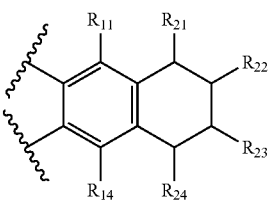

(XII)

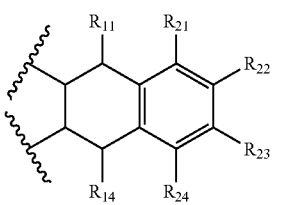

(XIII)

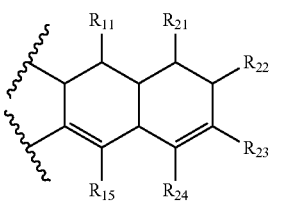

(XIV)

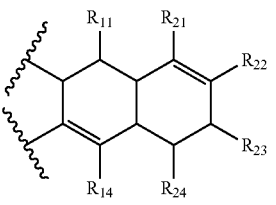

(XV)

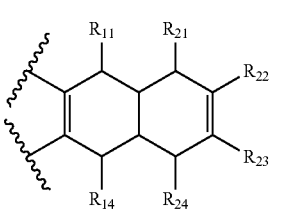

(XVI)

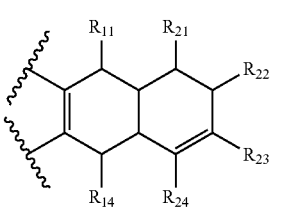

(XVII)

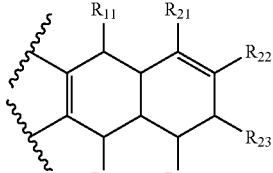

(XVIII)

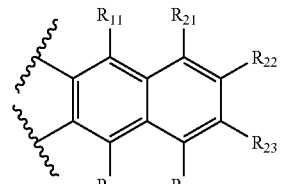

(XIX)

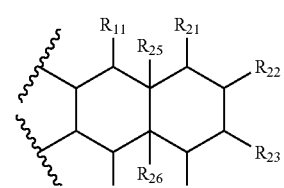

(XX)

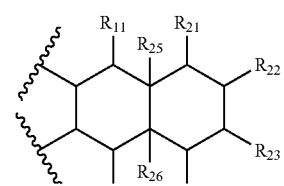

In the formulas, a wavy line "~~~" represents the quaternary amine section of the quaternary amine composition, shown in Formula III beginning with the $R_3$ functional groups. Formula XII and Formula XIII include a tetralin, where each of $R_1$, $R_2$, $R_7$, $R_{15}$, $R_{20}$, and $R_{10}$ is a carbon atom (C—) and each of $R_{16}$, $R_{17}$, $R_{18}$, and $R_{19}$ are a carbon bonded to a hydrogen (—CH) or where each of $R_1$, $R_2$, $R_7$, and $R_{10}$ are a carbon bonded to a hydrogen (—CH) and each of $R_{15}$, $R_{16}$, $R_{17}$, $R_{18}$, $R_{19}$, and $R_{20}$ is a carbon atom (C—). Formula XIX includes a naphthalene, where each of $R_1$, $R_2$, $R_7$, $R_{10}$, $R_{15}$, $R_{16}$, $R_{17}$, $R_{18}$, $R_{19}$, and $R_{20}$ is a carbon atom (C—). Formula XX includes a decalin where each of $R_1$, $R_2$, $R_7$, $R_{10}$, $R_{15}$, $R_{16}$, $R_{17}$, $R_{18}$, $R_{19}$, and $R_{20}$ is a carbon bonded to a hydrogen (—CH).

Returning to Formula III with reference to Formulas IX to XX, each of the functional groups $R_{11}$, $R_{14}$, $R_{21}$, $R_{22}$, $R_{23}$, $R_{24}$, $R_{25}$, and $R_{26}$ can be a hydrogen atom (H—), an aliphatic hydrocarbyl group, a substituted aliphatic hydrocarbyl group, and combinations of the same. The aliphatic hydrocarbyl group can include a saturated acyclic hydrocarbyl and an unsaturated acyclic hydrocarbyl. The saturated acyclic hydrocarbyl can be a saturated $C_1$-$C_{100}$ acyclic hydrocarbyl, alternately a saturated $C_1$-$C_{50}$ acyclic hydrocarbyl, alternately a saturated $C_1$-$C_{25}$ acyclic hydrocarbyl, alternately a saturated $C_1$-$C_{10}$ acyclic hydrocarbyl, alternately a saturated $C_2$-$C_{20}$ acyclic hydrocarbyl, and alternately a saturated $C_2$-$C_{10}$ acyclic hydrocarbyl. The unsaturated acyclic hydrocarbyl can be an unsaturated $C_1$-$C_{100}$ acyclic hydrocarbyl, alternately an unsaturated $C_1$-$C_{50}$ acyclic hydrocarbyl, alternately an unsaturated $C_1$-$C_{25}$ acyclic hydrocarbyl, alternately an unsaturated $C_1$-$C_{10}$ acyclic hydrocarbyl, alternately an unsaturated $C_2$-$C_{20}$ acyclic hydrocarbyl, and alternately an unsaturated $C_2$-$C_{10}$ acyclic hydrocarbyl.

The substituted aliphatic hydrocarbyl group can include a substituted saturated aliphatic hydrocarbyl group and a substituted unsaturated aliphatic hydrocarbyl group. The substituted aliphatic hydrocarbyl group can include a saturated acyclic hydrocarbyl group containing at least 1 carbon after substitution, alternately at least 2 carbons after substitution, alternately between 1 carbon and 19 carbons after substitution, and alternately between 1 carbon and 100 carbons after substitution. The substituted aliphatic hydrocarbyl group can include a replacement group, where the replacement group replaces one or more of the carbons in the substituted aliphatic hydrocarbyl group. The replacement group can include a hydroxyl group, an aminoalkyl group, an alkoxyl group, an alkylthio group, an amino group, a halo group, a haloalkyl group, a silyl group, a phosphoryl group, a sulfonyl group, and combinations of the same.

The functional groups $R_{11}$, $R_{14}$, $R_{21}$, $R_{22}$, $R_{23}$, $R_{24}$, $R_{25}$, and $R_{26}$ can be the same moiety, and alternately can be a different moiety. The moieties can result in the quaternary amine compositions having more than two tails.

The quaternary amine compositions can be synthesized by reacting an alkoxylated dimer diamine with a methyl halogen.

The methyl halogen can include methyl chloride, methyl iodine, and combinations of the same.

The alkoxylated dimer diamine can produce a non-ionic surfactant. The reaction of the alkoxylated dimer diamine with the methyl halogen can result in quaternary amines on the molecular backbone.

The reaction between the alkyoxylated dimer diamine and the methyl halogen can occur across a range of temperatures and pressures. In at least one embodiment, the reaction between the alkyoxylated dimer diamine and the methyl halogen can occur at ambient conditions.

The quaternary amine compositions produced by the described method can take the forms of Formula I, Formula II, and Formula III. In at least one embodiment, the quaternary amine composition can include the composition of Formula XXII:

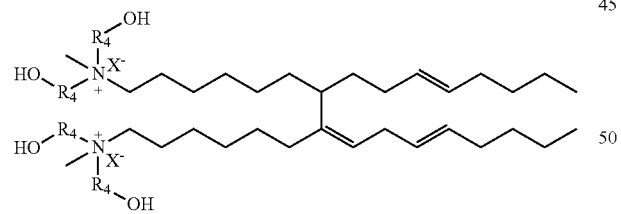

(XXII)

where the quaternary amine composition takes the form of Formula I; where $R_1$ is a carbon bonded to a hydrogen (—CH), $R_2$ is a carbon atom (C—), each $R_3$ is a saturated $C_6$ acyclic hydrocarbyl, $R_5$ is an unsaturated $C_8$ acyclic hydrocarbyl, $R_6$ is an unsaturated $C_8$ acyclic hydrocarbyl, and $R_4$ can include an acyclic hydrocarbyl, an acyclic heterohydrocarbyl, and combinations of the same.

In at least one embodiment, the quaternary amine composition can include the composition of Formula XXIII:

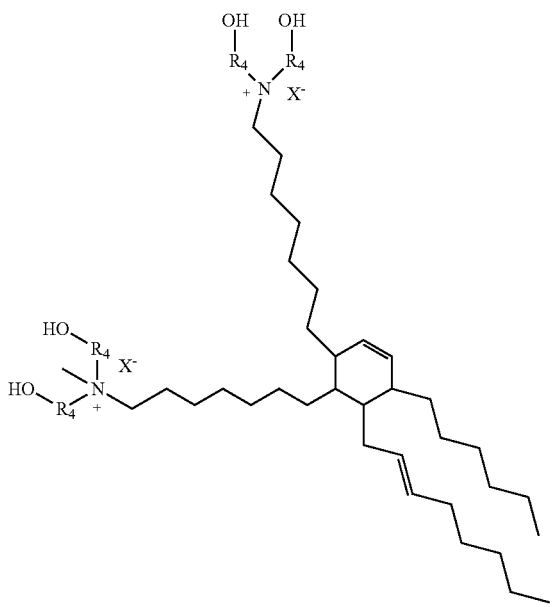

(XXIII)

where the quaternary amine composition takes the form of Formula II; where $R_1$, $R_2$, $R_7$, $R_8$, $R_9$, and $R_{10}$ form a cyclohexene ring, where each of $R_1$, $R_2$, $R_9$, and $R_{10}$ is a carbon bonded to a hydrogen (—CH), each of $R_7$ and $R_8$ is a carbon atom (C—), each $R_3$ is a saturated $C_7$ acyclic hydrocarbyl, $R_{13}$ is a saturated $C_6$ acyclic hydrocarbyl, $R_{14}$ is an unsaturated $C_8$ acyclic hydrocarbyl, and $R_4$ can include an acyclic hydrocarbyl, an acyclic heterohydrocarbyl, and combinations of the same.

In at least one embodiment, the quaternary amine composition can include the composition of Formula XXIV:

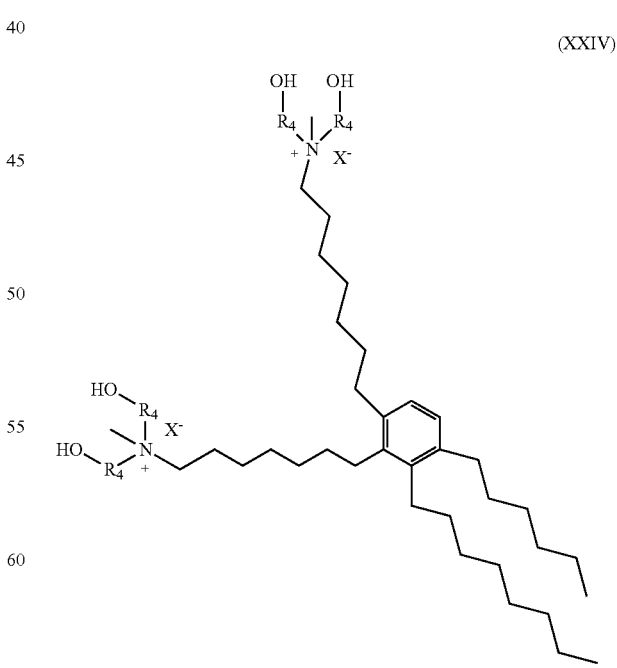

(XXIV)

where the quaternary amine composition takes the form of Formula II; where $R_1$, $R_2$, $R_7$, $R_8$, $R_9$, and $R_{10}$ form a benzene ring, where each of $R_1$, $R_2$, $R_7$, $R_8$, $R_9$, and $R_{10}$ is a carbon atom (C—), each $R_3$ is a saturated $C_7$ acyclic hydrocarbyl, $R_{13}$ is a saturated $C_6$ acyclic hydrocarbyl, $R_{14}$ is a saturated $C_8$ acyclic hydrocarbyl, and $R_4$ can include an acyclic hydrocarbyl, an acyclic heterohydrocarbyl, and combinations of the same.

In at least one embodiment, the quaternary amine composition can include the composition of Formula XXV:

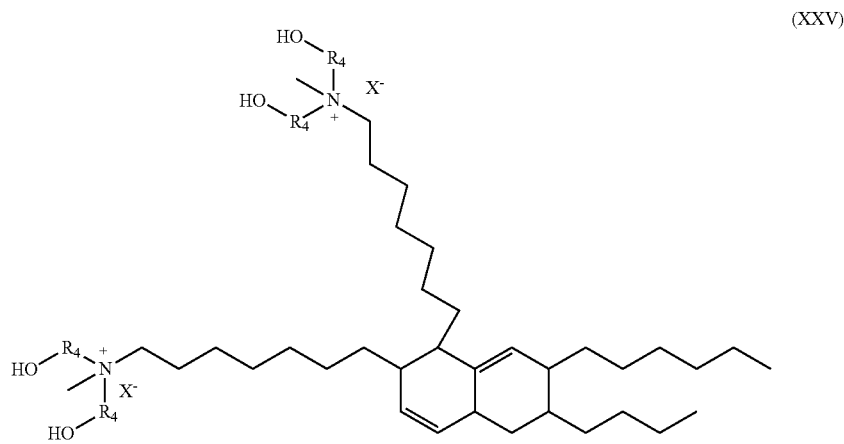

(XXV)

where the quaternary amine composition takes the form of Formula III; where $R_1$, $R_2$, $R_7$, $R_{15}$, $R_{20}$, and $R_{10}$ form a cyclohexene ring, where each of $R_1$, $R_2$, $R_{15}$, $R_{20}$, and $R_{10}$ is a carbon bonded to a hydrogen (—CH) and $R_7$ is a carbon atom (C—), the second ring is connected between $R_7$ and $R_{15}$, and $R_7$, $R_{16}$, $R_{17}$, $R_{18}$, $R_{19}$, and $R_{15}$ forms a cyclohexene ring, where $R_{16}$ is a carbon atom, each of $R_{17}$, $R_{18}$, and $R_{19}$ are carbon bonded to a hydrogen (—CH), each of $R_{21}$, and $R_{24}$ is a hydrogen atom (—H), $R_{22}$ is a saturated $C_6$ acyclic hydrocarbyl, $R_{23}$ is a saturated $C_4$ acyclic hydrocarbyl, and $R_4$ can include an acyclic hydrocarbyl, an acyclic heterohydrocarbyl, and combinations of the same.

In at least one embodiment, the quaternary amine composition can include the composition of Formula XXVI:

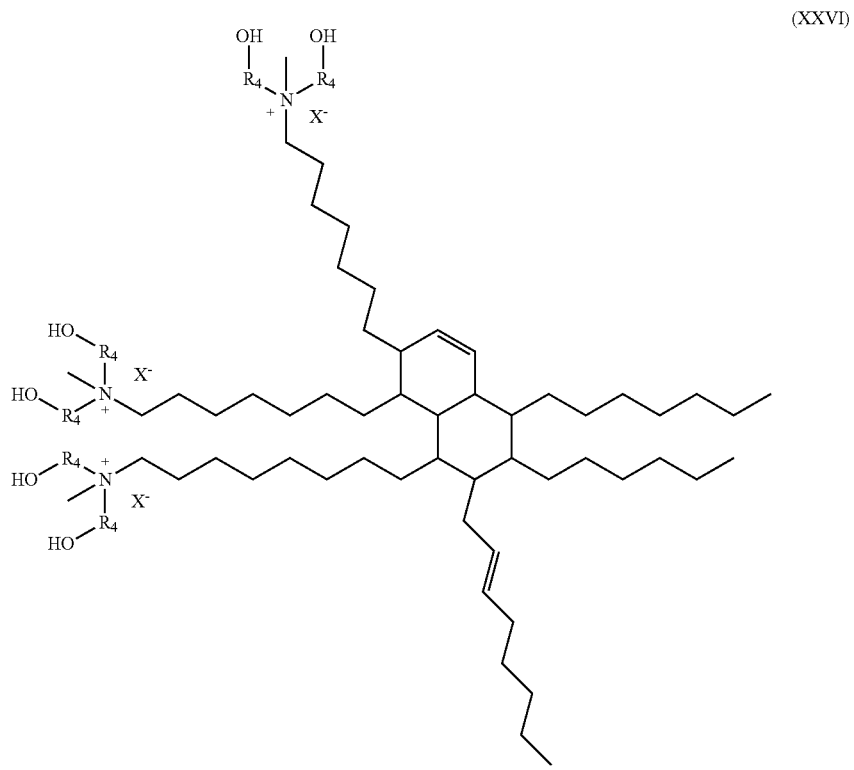

(XXVI)

where the quaternary amine composition takes the form of Formula III; where $R_1$, $R_2$, $R_7$, $R_{15}$, $R_{20}$, and $R_{10}$ form a cyclohexene ring, where each of $R_1$ and $R_2$ is a carbon bonded to a hydrogen (—CH), each of $R_7$, $R_{15}$, $R_{20}$, and $R_{10}$ is a carbon atom (C—), the second ring is connected between $R_{20}$ and $R_{10}$, and $R_{20}$, $R_{16}$, $R_{17}$, $R_{18}$, $R_{19}$, and $R_{10}$ forms a cyclohexane ring, where each of $R_{16}$, $R_{17}$, $R_{18}$, and $R_{19}$ are carbon bonded to a hydrogen (—CH), each of $R_{11}$, $R_{14}$, $R_{24}$, $R_{25}$, and $R_{26}$ is a hydrogen atom (—H), $R_{21}$ is a saturated $C_7$ acyclic hydrocarbyl, $R_{22}$ is a saturated $C_6$ acyclic hydrocarbyl, $R_{23}$ is an unsaturated $C_8$ acyclic hydrocarbyl, $R_{24}$ is a saturated acyclic heterohydrocarbyl having the form $C_8N(R_4)_2(OH)_2$ and $R_4$ can include an acyclic hydrocarbyl, an acyclic heterohydrocarbyl, and combinations of the same.

The quaternary amine compositions can reduce corrosion, can stabilize clay compounds, and can stabilize emulsions. Advantageously, the germinal-containing surfactants of the quaternary amine compositions have stronger adsorption, or binding strength, as compared to non-geminal quaternary amine surfactants.

The quaternary amine compositions can be used as additives in well fluids. The quaternary amine compositions can be added to the well fluids before introducing the well fluid to the well and alternately while the well fluid is being introduced to the well. The well fluids can include drilling fluids, fracturing fluids, completion fluids and combinations of the same. The well fluids can be aqueous-based fluids or oil-based fluids. The quaternary amine compositions can be mixed as an additive in a well fluid to produce an additive-containing well fluid. The quaternary amine surfactant can be present in the additive-containing well fluid in the range from 0.5 pounds per barrel (ppb) to 10 ppb. The additive-containing well fluid can be used to treat a wellbore. Treating a well can include reducing corrosion, stabilizing clays in the formation, stabilizing an emulsion, and combinations of the same.

In at least one embodiment, the quaternary amine composition can be added to an aqueous-based fluid for use as a well fluid to reduce corrosion by the aqueous-based fluid. The additive-containing well fluid can treat a wellbore, where a least a portion of the quaternary amine composition in the additive-containing well fluid is operable to contact a metal material in the wellbore. The metal material can include any type of metal suitable for use in a wellbore. Upon contact with metal material, the portion of the quaternary amine composition can form a film on the surface of the metal material. The film formed on the surface of the metal material can form a barrier to water. The film formed on the surface of the metal material can reduce corrosion of the metal material by preventing the well fluid from contacting the metal material. The film formed by the quaternary amine compositions can protect against any corrosive fluids. Examples of corrosive fluids include water, acids, bases, carbon dioxide, hydrogen sulfide, and combinations of the same.

In at least one embodiment, the quaternary amine composition can be added to an aqueous-based fluid for use as a well fluid to improve clay stabilization. The additive-containing well fluid can treat a wellbore wall, where at least a portion of the quaternary amine composition in the additive-containing well fluid is operable to contact a clay material in fluid contact with the wellbore wall. The clay material can include any kind of clay material found in a hydrocarbon-bearing formation. The clay material can be in the wellbore wall or in the hydrocarbon-bearing formation. On contact with the clay material, the portion of the quaternary amine composition can form a film on the clay material.

In at least one embodiment, the quaternary amine surfactant can be added to an oil-based fluid for use as a well fluid to stabilize the emulsion.

The quaternary amine compositions described here are positively charged and act as corrosion inhibitors. In contrast, the reactant alkoxylated dimer diamines can be used as secondary emulsifiers.

EXAMPLES

Example 1. Additive as Corrosion Inhibitor

Example 1 tested the quaternary amine composition as a corrosion inhibitor, using the quaternary amine composition of Formula I, having the specific form of Formula XXVII:

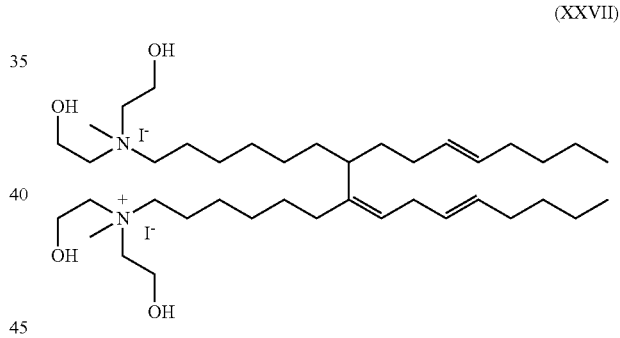

(XXVII)

where the quaternary amine composition takes the form of Formula XXII; where $R_1$ is a carbon bonded to a hydrogen (—CH), $R_2$ is a carbon atom (C—), each $R_3$ is a saturated $C_6$ acyclic hydrocarbyl, $R_5$ is an unsaturated $C_8$ acyclic hydrocarbyl, $R_6$ is an unsaturated $C_8$ acyclic hydrocarbyl, and each $R_4$ is a saturated $C_2$ acyclic hydrocarbyl.

Two 1018 steel coupons were tested, Coupon A and Coupon B. Each coupon was weighed to get an initial mass. Then each steel coupon was rolled in a vessel pressurized under 500 pounds per square inch (psi) carbon dioxide ($CO_2$) at 120 degree Fahrenheit (deg F.) for 16 hours in a two percent (2%) sodium chloride (NaCl) solution. Coupon A was untreated. Coupon B was treated with a 0.6% or 6 gallons per thousand gallons (gpt) dose rate of the quaternary amine composition of Formula XXVII. After testing, each coupon was cleaned according to API and NACE standards, including weighing each coupon to get a final mass. The results are shown in Table 1.

TABLE 1

Results of Example 1

| Coupon | Metal | Initial Mass (g) | Final Mass (g) | Mass Loss (g) | Surface Area (in²*) | Factor | Corrosion Loss (lb/ft²) |
|---|---|---|---|---|---|---|---|
| A (untreated) | 1018 Steel | 8.0157 | 7.27858 | 0.73712 | 1.4594 | 0.22 | 0.160 |
| B (treated) | 1018 Steel | 8.0179 | 7.825 | 0.1929 | 1.49433 | 0.21 | 0.041 |

*inches (in²)

The results show that the treatment of Coupon B with the quaternary amine composition reduced corrosion loss by nearly 400% and maintained Coupon B at less than the established failure criteria of less than 0.5 pounds per square foot (lb/ft²) corrosion loss. While Example 1 provides for a composition where the quaternary amine composition is added to an aqueous solution, the quaternary amine composition can be added to an oil composition.

Example 2. Additive as Clay Swelling Inhibitor

Example 2 compared different inhibitors for their clay swelling inhibition efficiency. The different inhibitors included the quaternary amine composition of Formula XXVII (Sample 2) and choline chloride (Sample 3). Choline chloride is an industry standard for inhibiting clay swelling and is considered to be an excellent performer. The two inhibitors were compared to a sample with no inhibitor (Sample 3). A fluid was prepared according to Table 2 for use in a clay swelling test. The fluid according to the composition of Table 1 was mixed for 5 minutes (min) and then allowed to remain static for 15 minutes (min). Then 5 milliliters (mL) were used for the clay swelling test. The clay swelling test was performed using a Fann model 440 Capillary Suction Timer (CST).

TABLE 2

Fluid Composition for Clay Swelling Test

| Component | Amount in Fluid |
|---|---|
| Water | 250 grams (g) |
| Bentonite | 5.1 g |
| Silica Flour | 24.9 g |
| Inhibitor | 5 mL |

The results from the clay swelling test are shown in Table 3.

TABLE 3

Results of Example 2.

| Sample | Time (s) normalized |
|---|---|
| 1 (No inhibitor) | 482.8 |
| 2 (Quaternary Salt) | 1.7 |
| 3 (Choline Chloride) | 2.9 |

The results show that the quaternary amine composition is efficient at inhibiting clay swelling and can be used as a clay control agent. A CST value of less than 50 seconds (s) is considered to have excellent efficiency at inhibiting clay swelling. In general, the lower the value, the better the performance of the inhibitor. Each of the Examples illustrate that the quaternary amine composition can be used to improve production fluids.

Although the technology has been described in detail, it should be understood that various changes, substitutions, and alterations can be made hereupon without departing from the principle and scope. Accordingly, the scope of the embodiments should be determined by the following claims and their appropriate legal equivalents.

The singular forms "a," "an," and "the" include plural referents, unless the context clearly dictates otherwise.

Optional or optionally means that the subsequently described event or circumstances can or may not occur. The description includes instances where the event or circumstance occurs and instances where it does not occur.

Ranges may be expressed as from one particular value to another particular value. When such a range is expressed, it is to be understood that another embodiment is from the one particular value to the other particular value, along with all combinations within said range.

Throughout this application, where patents or publications are referenced, the disclosures of these references in their entireties are intended to be incorporated by reference into this application, in order to more fully describe the state of the art, except when these references contradict the statements made here.

As used here and in the appended claims, the words "comprise," "has," and "include" and all grammatical variations thereof are each intended to have an open, non-limiting meaning that does not exclude additional elements or steps.

What is claimed is:

1. A quaternary amine composition comprises Formula I, where Formula I is:

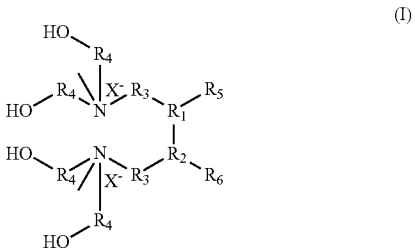

where:
each of $R_1$ and $R_2$ is selected from the group consisting of a carbon atom (C—) and a carbon bonded to a hydrogen (—CH),
each $R_3$ is selected from the group consisting of a saturated aliphatic hydrocarbyl and an unsaturated aliphatic hydrocarbyl,
each $R_4$ is selected from the group consisting of an acyclic hydrocarbyl and an acyclic heterohydrocarbyl,
each of $R_5$ and $R_6$ is selected from the group consisting of a saturated acyclic hydrocarbyl and an unsaturated acyclic hydrocarbyl, X is selected from the group consisting of an iodine ion (I—), a chlorine ion (Cl—), and combinations of the same.

2. The quaternary amine composition of claim 1, where $R_3$ is selected from the group consisting of a saturated $C_2$-$C_{20}$ acyclic hydrocarbyl and an unsaturated $C_2$-$C_{20}$ acyclic hydrocarbyl.

3. The quaternary amine composition of claim 1, where at least one of $R_5$ and $R_6$ is an unsaturated $C_2$-$C_{20}$ acyclic hydrocarbyl.

4. The quaternary amine composition of claim 1, where both $R_5$ and $R_6$ are unsaturated $C_2$-$C_{20}$ acyclic hydrocarbyls.

5. The quaternary amine composition of claim 1, where $R_3$ is a saturated $C_5$-$C_{10}$ acyclic hydrocarbyl and each of $R_5$ and $R_6$ is a $C_5$-$C_{15}$ acyclic hydrocarbyl.

6. The quaternary amine composition of claim 1, where the substituted aliphatic hydrocarbyl group comprises a replacement group, where the replacement group is selected from the group consisting of a hydroxyl group, an aminoalkyl group, an alkoxyl group, an alkylthio group, an amino group, a halo group, a haloalkyl group, a silyl group, a phosphoryl group, a sulfonyl group, and combinations of the same.

7. The quaternary amine composition of claim 1, comprising Formula I:

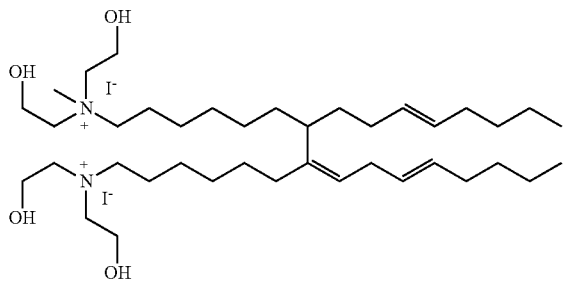

(XXVII)

where the quaternary amine composition takes the form of Formula I; where $R_1$ is a carbon bonded to a hydrogen (—CH), $R_2$ is a carbon atom (C—), each $R_3$ is a saturated $C_6$ acyclic hydrocarbyl, $R_5$ is an unsaturated $C_8$ acyclic hydrocarbyl, $R_6$ is an unsaturated $C_8$ acyclic hydrocarbyl, and each $R_4$ is a saturated $C_2$ acyclic hydrocarbyl.

8. The quaternary amine composition of claim 1, further comprising an additional quaternary amine composition selected from the group consisting of Formula II, Formula III, and combinations of the same, where Formula II is:

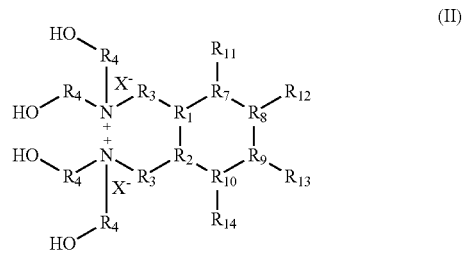

(II)

where:

each of $R_7$, $R_8$, $R_9$, and $R_{10}$ is selected from the group consisting of a C— and a —CH, each of $R_{11}$, $R_{12}$, $R_{13}$, and $R_{14}$ is selected from the group consisting of a hydrogen atom (H—), an aliphatic hydrocarbyl group, and a substituted aliphatic hydrocarbyl group;

where Formula III is:

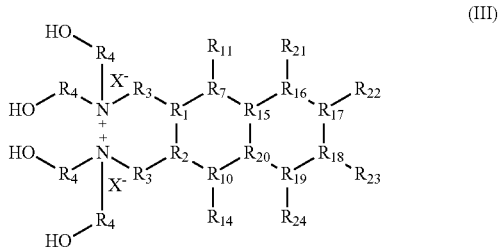

(III)

$R_{15}$ is selected from the group consisting of a C—, a —CH, and a carbon bonded to $R_{25}$ (—$CR_{25}$), each of $R_{16}$, $R_{17}$, $R_{18}$, and $R_{19}$ is selected from the group consisting of a C— and a —CH, $R_{20}$ is selected from the group consisting of a C—, a —CH, and a carbon bonded to $R_{26}$ (—$CR_{26}$), each of $R_{21}$, $R_{22}$, $R_{23}$, and $R_{24}$ can include a hydrogen atom (H—), an aliphatic hydrocarbyl group, and a substituted aliphatic hydrocarbyl group, $R_{25}$ is selected from the group consisting of an aliphatic hydrocarbyl group, a substituted aliphatic hydrocarbyl group, and combinations of the same, $R_{26}$ is selected from the group consisting of an aliphatic hydrocarbyl group, a substituted aliphatic hydrocarbyl group, and combinations of the same.

* * * * *